(12) United States Patent
Fenton

(10) Patent No.: US 7,767,195 B2
(45) Date of Patent: Aug. 3, 2010

(54) METHOD FOR INDUCING A PSYCHOTIC STATE IN AN ANIMAL AND A HIGH THROUGHPUT ASSAY METHOD FOR IDENTIFYING A CANDIDATE AGENT HAVING ANTI-PSYCHOTIC PROPERTIES

(75) Inventor: Andre A. Fenton, New York, NY (US)

(73) Assignee: The Research Foundation of State University of New York, Albany, NY (US)

( * ) Notice: Subject to any disclaimer, the term of this patent is extended or adjusted under 35 U.S.C. 154(b) by 384 days.

(21) Appl. No.: 11/801,063

(22) Filed: May 8, 2007

(65) Prior Publication Data

US 2007/0274920 A1 Nov. 29, 2007

Related U.S. Application Data

(60) Provisional application No. 60/798,617, filed on May 8, 2006.

(51) Int. Cl.
| | |
|---|---|
| *A61K 49/00* | (2006.01) |
| *A61K 31/42* | (2006.01) |
| *A61K 31/166* | (2006.01) |
| *A61K 35/60* | (2006.01) |
| *A61B 5/0484* | (2006.01) |
| *C07D 261/12* | (2006.01) |
| *C07C 233/06* | (2006.01) |

(52) U.S. Cl. ............. 424/9.2; 600/373; 514/380; 514/613; 514/816; 514/267; 424/537; 548/243; 564/123

(58) Field of Classification Search .............. None
See application file for complete search history.

(56) References Cited

OTHER PUBLICATIONS

Olypher Av et al. Cognitive disorganization in hippocampus: a physiological model of the disorganization in psychosis. J Neuroscience, Jan. 4, 2006; 26(1):158-168.*

Wesierska M et al. Beyond memory, navigation, and inhibition: behavioral evidence for hippocampus-dependent cognitive coordination in the rat. J Neuroscience. Mar. 2, 2005; 25(9):2413-2419.*

* cited by examiner

*Primary Examiner*—Elizabeth C. Kemmerer
*Assistant Examiner*—Kimberly A. Ballard
(74) *Attorney, Agent, or Firm*—Dilworth & Barrese, LLP

(57) ABSTRACT

A high throughput neurophysiological assay for identifying anti-psychotic compounds is disclosed. In particular, a high throughput neurophysiological assay using information obtained from injecting a neural activity blocker, such as tetrodotoxin (TTX), into one hippocampus persistently coactivated pyramidal cells in the uninjected hippocampus that initially discharged independently. In accord with the definition of cognitive disorganization, pyramidal cell firing rates only changed for 15 min and did not accompany the coactivation. The disclosed assay uses the TTX-induced coactivity of hippocampal pyramidal cell discharge to identify compounds that may prevent or attenuate the changes in the hippocampal pyramidal cell discharge observed when a neural activity blocker is administered. The assays of the invention are useful for high throughput screening of targets in the discovery of drugs that have anti-psychotic properties. Also disclosed is a method of inducing and measuring neural activity normally associated with a psychotic state.

16 Claims, 7 Drawing Sheets

CABLE

14

METHOD FOR INDUCING A PSYCHOTIC STATE IN AN ANIMAL AND A HIGH THROUGHPUT ASSAY METHOD FOR IDENTIFYING A CANDIDATE AGENT HAVING ANTI-PSYCHOTIC PROPERTIES

CROSS REFERENCE TO RELATED APPLICATIONS

This application claims priority to U.S. provisional application Ser. No. 60/798,617 filed May 8, 2006, which is herein incorporated by reference.

FIELD OF THE INVENTION

The present invention relates to a method for inducing a psychotic state in an animal and a high throughput assay method for identifying a candidate agent having anti-psychotic properties.

BACKGROUND OF THE INVENTION

A very large percentage of the international population is affected with some sort of psychotic disorder that if left undiagnosed and untreated could result in injury to the person with the disorder and/or to people associated and/or close to the person with the disorder. Diagnosis of a psychological disorder can often take time to properly diagnose with only a handful of approved drugs available to treat such disorders once diagnosed. Almost every physician would agree that additional drugs are needed in order to properly treat the vast array of psychological disorders in the international population today and in the future. However, conventional methods of determining the anti-psychotic properties of a candidate agent are often time consuming and costly. Many times candidate agents are merely slight chemical manipulations of existing anti-psychotic agents in order to make them either more effective or last longer. Very few "new" candidates that are totally different from existing drugs ever make it to the discovery stage since most of the money and focus is tied up in the aforementioned chemical manipulation of a know anti-psychotic agents. In fact, in 2005 a NIH-funded study found that treatment with contemporary antipsychotics was no more effective that with the drugs that were introduced up to 40 years ago.

Once a researcher makes or designs a new compound or manipulates an old compound in such a way that it might have anti-psychotic properties, the compound must go through a basic level of screening to determine whether the new compound actually has anti-psychotic properties. This is often a behavioral based study and can take extensive periods of time to observe the behavior of animals, such as rats, before and after being administered the new compound, to make the determination whether the experimental compound actually processes anti-psychotic properties. This is time consuming and expensive.

Moreover, in order to check whether a compound actually has anti-psychotic capabilities an animal model having psychotic tendencies must be maintained so that it can be determined whether behavioral attributes associated with psychotic disorders of the model disappear or are attenuated once the experimental compound is administered. Therefore, what is needed is a fast, inexpensive way for research scientists to assay many chemical compounds and segregate the most promising candidates more quickly and less expensively so that more candidate agents are available for the next stage of development. In particular, what is needed is a high throughput assay, which will allow many compounds to be assayed over a short period of time, less expensively than traditional "inject and observe" behavioral methods. The present invention provides such an assay that overcomes the shortcomings of the prior methods.

SUMMARY OF THE INVENTION

The present invention is directed to a high throughput assay method for identifying a candidate agent having anti-psychotic properties. In particular, the high throughput assay method of the present invention comprises the following steps:

a) adding an effective amount of neural activity blocker to a first portion of a hippocampus of an animal subject that is substantially opposite from a second portion of the hippocampus having extra-cellular recording electrodes positioned therein for recording discharge of an ensemble of neurons;

b) continuously recording neural activity in the second portion of the hippocampus for a predetermined amount of time before and after step a);

c) administering a predetermined amount of at least one candidate agent to the animal subject either directly to the brain, by oral administration or by systemic injection during a predetermined period of time that could begin either long or shortly before step a) or after step a), depending on the candidate agent's presumed properties. For example, administration can be done for as long as up to several months before or for as short as several hours before;

d) measuring the number of neurons in the second portion of the hippocampus that discharge coactively after adding the effective amount of neural activity blocker to the first portion of the hippocampus and again after adding the candidate agent of step c) to the animal subject;

e) measuring the probability of neurons in the second portion of the hippocampus that discharge coactively after adding the effective amount of neural activity blocker to the first portion of the hippocampus. This probability, measured in animal subjects that receive a control treatment that lacks the candidate agent, is compared to the probability that is observed in subjects that are treated with the candidate agent; and f) correlating a decrease in the probability of neurons firing coactively as determined in step e) with a candidate agent having anti-psychotic properties.

The present invention is also directed to a model for inducing a psychotic state. That is, a model that induces and measures neural activity that is normally associated with various psychotic disorders. In particular, the present invention is directed to a method of inducing and measuring neural activity normally associated with a psychotic state comprising the following steps:

a) adding an effective amount of neural activity blocker to a first portion of a hippocampus of an animal subject located substantially opposite from a second portion of the hippocampus having extra-cellular recording electrodes positioned therein for recording discharge of an ensemble of neurons;

b) continuously recording neural activity in the second portion of said hippocampus for a predetermined amount of time before and after step a);

c) measuring the number of neurons in the second portion of the hippocampus that discharge coactively after adding the effective amount of neural activity blocker to the first portion of said hippocampus; and d) correlating an increase of the number of neurons that discharge coactively as determined in step c) with an induced psychotic state.

Variations and additions to the methods described above are also part of the present invention and are described in greater detail in the Detailed Description of the Invention section including the examples and figures below.

BRIEF DESCRIPTION OF THE FIGURES

FIG. 1 provides an example used to illustrate subgrouping and contextual modulation of perception.

DETAILED DESCRIPTION OF THE INVENTION

Figure 2:
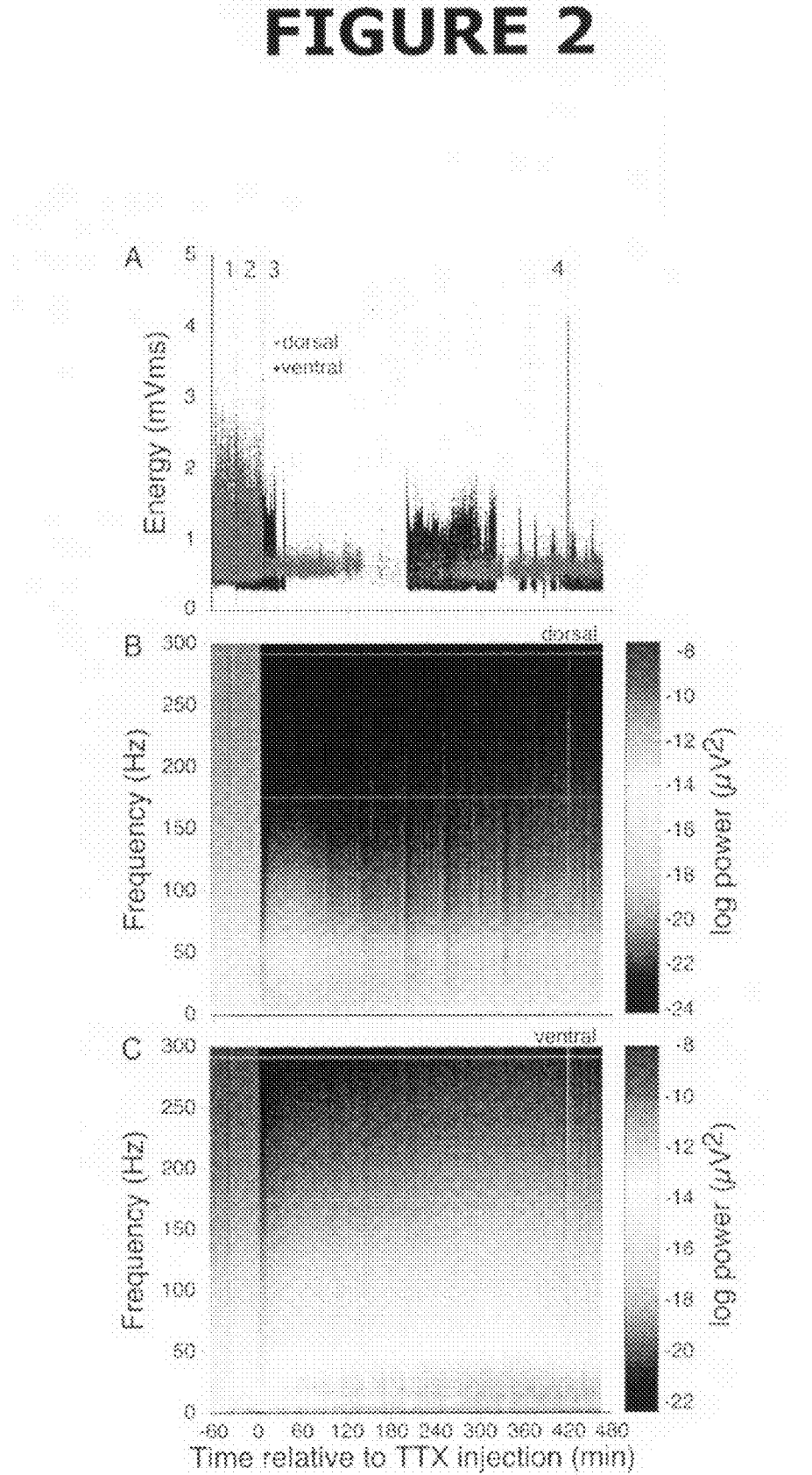
FIG. 2 provides a graphical representation of the effect on neural activity in the injected hippocampus of injecting the neural activity blocker TTX.

The brain selectively activates and suppresses representations it encodes. This neural coordination has been called cognitive coordination. It is defined as the set of neural processes that control the timing of spiking amongst cells without changing individual response properties. The coordination idea developed from the binding problem. If bound stimulus features were represented by cell assemblies then without segregation, coactivation of overlapping assemblies, could lead to false, inappropriate, or confused activations of neural representations. One proposed mechanism of segregation is desynchronization on the timescale of gamma oscillations.

Figure 1:
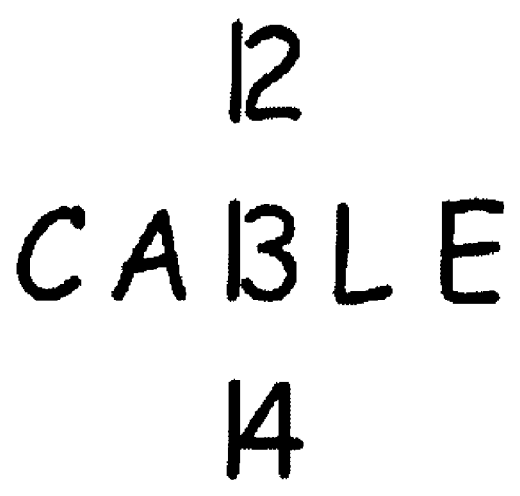

Cognitive coordination is inferred when people distinguish between relevant and irrelevant stimuli to group the relevant stimuli into a coherent percept according to contextual demands. For example, if instructed to identify words, in the example given in FIG. 1, one is likely to segregate the relevant letters from the numbers and associate the central symbol with the letters to form the word "cable". The central symbol is perceived as the letter 'B' or the number 13 depending on whether words or number sequences are the target. The term "subgrouping" is used to refer to segregating relevant from irrelevant stimuli and selectively using associations amongst the relevant stimuli.

Schizophrenic subjects are especially impaired in subgrouping tasks suggesting impaired cognitive coordination, also called cognitive disorganization, is the core deficit in disorganized schizophrenia, a condition characterized by hallucinations, disorganization, and thought disorder. In strong support of the proposal, synchrony is altered in the electroencephalogram (EEG) of schizophrenic subjects. The alterations positively correlated with the severity of hallucinations, conceptual disorganization, and thought disorder.

One rat study done in 2005 provided indirect evidence that injecting the neural activity blocker tetrodotoxin (TTX) into one hippocampus specifically impaired cognitive coordination. In this study, rats placed on a continuously rotating arena were challenged to subgroup environmental stimuli into relevant, stationary room cues distinct from rotating cues. The rats had to represent space using stationary cues to avoid the region of the room where there was foot-shock. The TTX injection selectively impaired avoidance in this task but not in tasks that did not require subgrouping to selectively associate shock with the current location. While impaired cognitive coordination explained the results, impaired memory, navigation or behavioral inhibition could not. The present invention advances this study to the next level and demonstrates and claims that administering a neural activity blocker, such as TTX, muscimol, lidocaine, or any other local anesthetics, to one portion of the hippocampus in an animal subject impairs cognitive coordination in the un-injected portion of the hippocampus.

In particular, the present invention is directed to a high throughput assay method for identifying a candidate agent having anti-psychotic properties wherein a neural activity blocker, such as TTX, is added to one portion of an animal subject's hippocampus thereby changing the timing of discharge amongst hippocampal neurons while preserving firing rates. Confounding the TTX-induced dynamic changes in discharge with those associated with the rat's motor, cognitive or perceptual activity was avoided in the present invention by using urethane-anesthetized rats for the assay.

As stated above and demonstrated herein, in the brain, cognitive representations of external stimuli and thoughts ("events") are reflected in patterns of neural electrical discharge. Different events are associated with the electrical activation of different subgroups of neurons. Thus, neurons that are reliably coactive are functionally coupled and tend to represent a particular event, while neurons that activate independently are not functionally coupled and tend to represent distinct independent events. Usually the brain increases the coupling of neurons in distinct representations if the events are experienced together or if they have common or related elements. The manipulations that cause a general, random increase in the coactivation of uncoupled neurons will cause distinct representations to merge or interfere with each other leading to confusion, delusion, hallucination and general disorganization of thought. It is noted that this is not really a new idea, and that the aforementioned consequences are the core symptoms of psychosis associated with diseases like schizophrenia.

However, the present invention uses a novel way to experimentally cause functionally uncoupled neurons in the rat brain to reliably coactivate, while leaving undisturbed the coactivity of the already (appropriately) coupled neurons. This manipulation induced phenomena and disorganized behavior is caused by a general, random increase in the coactivation of uncoupled neurons which causes distinct representations to merge or interfere with each other leading to confusion, delusion, hallucination and general disorganization of thought. That is, these findings are the basis for the high throughput assay method for identifying a candidate agent having anti-psychotic properties as well as the method of inducing and measuring neural activity normally associated with a psychotic state of the present invention. The high throughput physiological assay can be valuable for anti-psychotic drug discovery as well as used in research in general. The high throughput neurophysiological assay of the present invention is described below.

In one embodiment of the present invention, the high throughput physiological assay for determining the anti-psychotic potential of a candidate agent of the present invention is described below using the following steps:

1) deeply anesthetize an animal, such as a rat, using anesthesia that will last several hours. In one embodiment of the present invention, 125 g/kg of 20% urethane is used to anesthetize a Long-Evans rats for the assay;
2) performing standard stereotaxic brain surgery to make a craniotomy above the hippocampus which will permit the implantation of standard extracellular recording electrodes to one portion of the hippocampus of the animal;
3) lowering extracellular recording electrodes to the one portion of the hippocampus cell layer so as to record the discharge of an ensemble of neurons. In one embodiment of the present invention, tetrode configured electrodes are used since it has been determined that each tetrode configured electrode can record 5-10 neurons simultaneously. Other types of electrodes can be used, however, whatever electrode is chosen the electrode should be able to record from as many cells as possible, preferably between about 4 to about 12 neurons simultaneously;
4) using standard methods to classify individual extracellular events as having unitary wave shape and thus originating from a single neural source. Once this is accomplished, only the time of the discharge events will be used in the assay;
5) recording in this fashion continuously for a predetermined period of time, preferably for about thirty minutes, so as to ensure stability of the recordings and neural activity;
6) adding at least one neural activity blocker in a physiological solution, such as tetrodotoxin (TTX) in a saline solution, into a portion of the hippocampus opposite the portion of the hippocampus having the recording electrodes. In one embodiment of the present invention, about 5 ng of TTX in about 1 μl saline solution is injected using a Hamilton syringe. The injection may also accomplished stereotaxically using a fine needle such as a 30-gauge hypodermic tubing injecting the neural activity blocker over a period of about 2 minutes. The injection of the neural activity blocker stops activity in the portion of the hippocampus in which the blocker was injected, which subtly disinhibits the other portion of the hippocampus from which the neural activity is being recorded. Ultimately, this causes neurons that discharged independently to functionally couple and fire coactively. The change in the amount of neurons that were discharging independently prior to administering the neural activity blocker to functionally coupling and firing coactively after the blocker is administered can be measured using any statistical correlation method, such as, the Pearson correlation calculation technique, the Kendall correlation calculation technique or the arbitrary variants of any mathematical correlation technique. In one embodiment of the present invention, the Kendal correlation was used to measure between all pairs of spike trains at 5-minute intervals. The subset of spike train pairs that were stably uncorrelated before the TTX injection are designated the initially uncoupled subset and the remaining spike train pairs are designated the initially coupled subset. In this embodiment, it was observed that after the TTX injection, the correlations amongst the initially uncoupled subset increased while correlations in the initially coupled subset did not change. In the TTX-induced animal functional coupling occurred within 30-40 minutes of the injection and lasted many hours. Coactivity can also be accomplished by administering the drug phencyclidine (PCP), which is a potent psychotomimetic. There are, therefore, multiple ways to induce the physiological state of increased functional coupling in neurons that were stably uncoupled, all of which can be used to form the basis of the assay of the present invention;

7) administering a predetermined amount of at least one candidate agent to the animal subject either directly to the brain, by oral administration or by systemic injection during a predetermined amount of time before or after the injection of the neural activity blocker;
8) measuring as in step 6) the change in the probability of neurons discharging independently and the probability of neurons coupling and firing coactively in an animal subject that received the drug candidate and comparing the corresponding change in a control animal subject that did not receive the drug candidate;
9) comparing the probability of neurons in the portion of the hippocampus having the recording electrode that discharge coactively after adding an effective amount of neural activity blocker to the portion of the hippocampus opposite the portion of the hippocampus having the electrodes with the proportion of neurons that discharge coactively after adding the candidate agent to the animal subject; and
10) correlating a decrease or attenuation in the number of neurons firing coactively as determined in step 9) with a candidate agent having anti-psychotic properties.

The assay of the present invention is based on the hypothesis that identifies aberrantly increased coupling as the underlying cause of psychotic symptoms, an effective anti-psychotic will selectively prevent or attenuate the experimentally (TTX)-induced increase of functional coupling. In addition, the present invention also describes that the TTX injection induces a behavioral disorganization in rats that is specific and predicted by the hypothesis that the TTX induces disorganization as seen in psychosis. However, the assay based on aberrantly increased coupling discussed above is less labor intensive than a similar behavioral assay for the efficacy of an anti-psychotic. An effective anti-psychotic candidate would block or attenuate the TTX-induced behavioral disorganization.

The above-described physiological model and assay is the first physiological model for psychosis and the first physiological assay for anti-psychotic efficacy. The assay described above can be performed in one afternoon whereas preclinical assays rely on behavioural analyses and do not reveal anything about the mechanisms of the compound action. The physiological assay described here is reliable and relatively easy to induce and record. One embodiment of the present invention can be achieved according to the materials and methods used to develop and practice the physiological model for psychosis, develop and practice the physiological assays for anti-psychotic efficacy described below.

Materials and Methods

Electrophysiology

All procedures met institutional and NIH guidelines. Rats were mounted in a stereotaxic instrument under urethane (1.25 g/kg) anesthesia, which was supplemented as necessary. A 30-gauge cannula used for intrahippocampal injections in awake rats was lowered into one hippocampus with a micromanipulator. The same injection site (relative to bregma: AP−3.5; ML±2.6; DV−3.5) and similar procedures were used as in the behavioural experiments. TTX (5 ng/μl saline) or saline was injected during 1 minute unless stated otherwise. The electrophysiological methods were only slightly modified from those used to record from awake rats. Instead of implanting tetrodes in microdrives, the tetrodes were lowered to the recording targets by stereotaxic micromanipulators.

Single Unit Analyses

Figure 3:
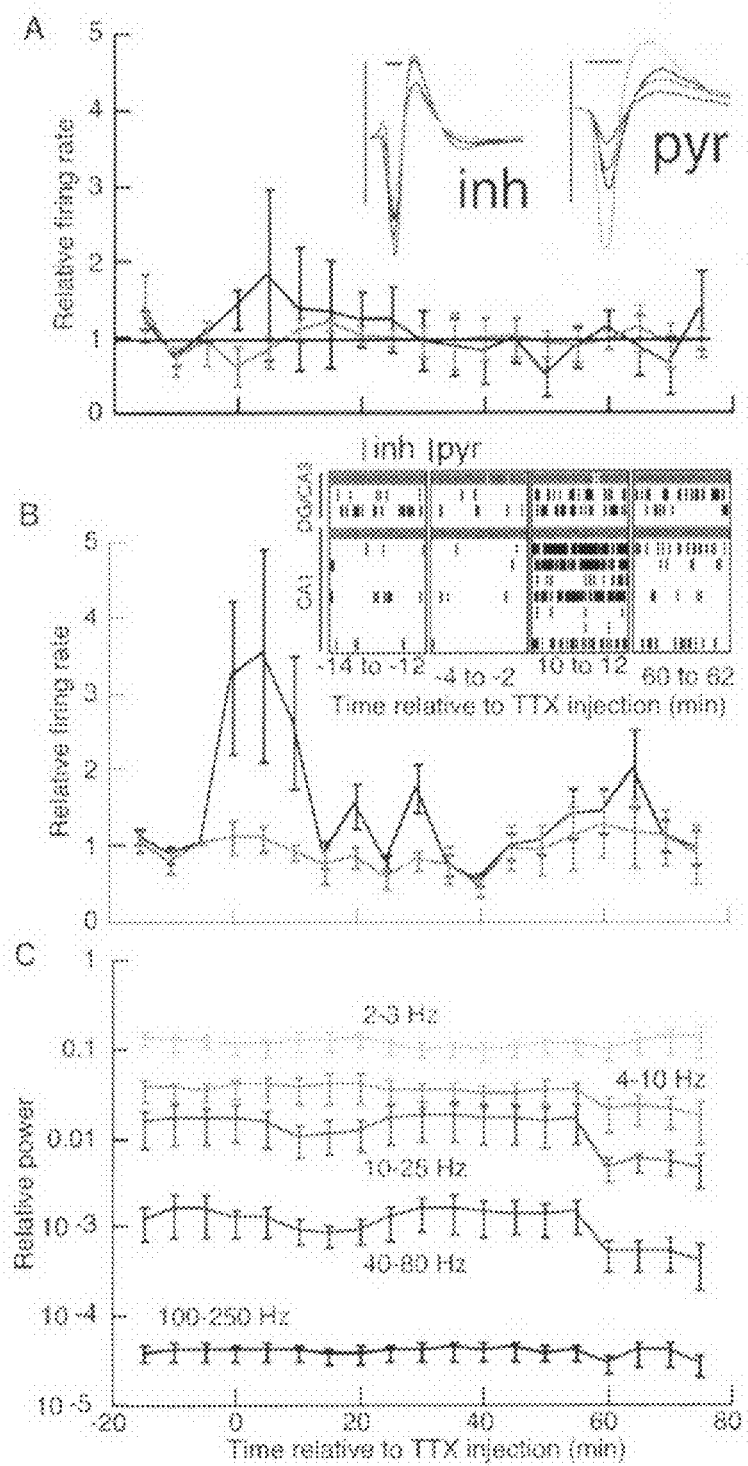
FIG. 3 provides a graphical representation of the effect on neural activity in the un-injected hippocampus of injecting the control solution of saline or the neural activity blocker TTX.

Single units with long duration action potentials (>350 μs) and low (<1 AP/s) firing rates were distinguished from those with brief action potentials (<350 μs) and high (>1 AP/s) firing rates, criteria corresponding to the putative classification of hippocampal pyramidal cells and interneurons, respectively (FIG. 3). Only recordings in which action potential waveforms were stable for >2 hours were analysed (20 of 26 rats). Data were divided into 5-min intervals relative to the TTX injection. Changes were measured relative to baseline taken as the value from the 5-min immediately before injection.

The correlations between the discharges of pairs of simultaneously recorded cells were calculated. Spike counts in fixed duration time bins were computed and the non-parametric Kendall's correlation coefficient τ was calculated. The time bin durations were 5, 10, 25, 50, 100, 250, and 500 ms.

Spectra of local field potentials (LFPs) were analysed for power in the delta (2-3 Hz), theta (4-10 Hz), beta (10-25 Hz), gamma (40-80 Hz), and sharp wave-associated ripple (100-250 Hz) frequency bands relative to the power between 1-300 Hz. All data are reported as averages±s.e.m.

Neural Network Model

A Hopfield-type network was adopted to model the conditions requiring cognitive coordination of dissociated room and arena spatial information:

$$\tau \frac{dh_i}{dt} = -h_i(t) + \sum_{j=1}^{N} (w_{ij} - w^{INH}) \cdot r_j(t) + I_i(t), \ 1 \le i \le N, \quad (1)$$

$$r_i(t) = \frac{1}{1 + \exp(-2\beta(h_i(t) - \alpha_i))}, \quad (2)$$

$$\alpha_i = \begin{cases} \alpha^{HIGH}, & r_i(t - \delta t) < \gamma, \\ \alpha^{LOW}, & r_i(t - \delta t) \ge \gamma, \end{cases} \quad (3)$$

where $h_i(t)$ and $r_i(t)$ represent respectively the activation and the rate of the i-th cell, $\tau=10$ ms, $\alpha^{HIGH}=0$, $\alpha^{LOW}=-2.5$, $\beta=3.5$, $\gamma=0.5$, $w^{INH}=0.32$, $\delta t=0.1$ ms, $N=732$. External input $I_i(t)$ was either absent or it set the cell's discharge to a rate corresponding to the rat's location in the cell's firing field. Firing fields were modeled as 2D Gaussians:

$$r_i(t) = p_i \cdot a_i \exp(-\|f_i - x^{RAT}(t)\|^2 / 2\sigma_i^2). \quad (4)$$

Here $a_i=0.9$, $\sigma_i=10$ cm for all the cells, $\|\cdot\|$ is the standard Euclidean distance, $f_i$ and $x^{RAT}$ are the locations of the cell's firing field center and the rat, respectively. The firing fields of half the cells were defined in the coordinate frame of the room (i=1, ..., $N_{room}$, $N_{room}=316$). For these "room cells", both $f_i$ and $x^{RAT}$ in Eq. 4 were specified in room coordinates. The other half ($N_{room}+1 \le i \le N, N=732$; "arena cells") had fields defined in the coordinate frame of a constantly rotating arena (1 rpm).

Without external input ($p_i=0$) a cell's activity was determined by the activity of all the cells in the network in accord with Eqs. 1-3. When external input corresponded to room locations, $p_i$'s for 90% of randomly chosen room cells were set to 1 for as long as the input lasted and 0 otherwise. When external input corresponded to arena positions, $p_i$'s for 90% of randomly chosen arena cells were set to 1. In the case of the input representing both frames, $p_i$'s were non-zero for some room and arena cells. For example, in FIG. 7C, $p_i$'s were equal to 0.55 for 90% of randomly chosen room cells and $p_i$'s were equal to 0.45 for 90% of randomly chosen arena cells. For all the other cells in the network $p_i$'s were equal to zero.

The weights $w_{ij}$ of connections between cells with fields in the same frame were defined to be strong for pairs of cells with adjacent firing field centers and weak for pairs of cells with distant firing field centers: $w_{ij} = \exp(-\|f_i - f_j\|^2/100)$, $1 \le i, j \le N_{room}$, or $N_{room}+1 \le i, j \le N$. The weights between room and arena cells were relatively weak, $w_{ij}=\zeta$, where $\zeta$ was a random number from the interval (0, 0.25). To study the effect of randomly increasing excitatory connections in the network the weights were corrupted according to one of two models:

$$w_{ij}^{(1)} = w_{ij} + p \cdot \eta, \quad (5a)$$

$$w_{ij}^{(1)} = w_{ij} + p \cdot (1 - w_{ij}) \eta, \quad (5b)$$

where p set the magnitude of the maximal change, and η was a random number from the interval (0,1). For the "symmetric" version of the network we required not just the usual symmetry of weights $w_{ij}=w_{ji}$ for $1 \le i \le j \le N$ but also the identity of weights between the room cells and weights between the arena cells: $w_{ij}=w_{i+N_{room}, j+N_{room}}$ for $1 \le i, j \le N_{room}$ to balance both representations. The difference between the symmetrized and original weights was small and random. Due to that, in accord with theory (Amit, 1989), the networks with symmetrized weights behaved similar to the networks with non-symmetric weights. For the symmetric network we calculated the energy function as defined in Hopfield (1984) and made sure that the stabilization of network activity corresponded to a monotonic decrease of the energy function toward a local minimum.

To assess what magnitudes of weight corruption p caused failures of the network to switch from the representation of one location to the representation of another, we chose a set of seven distributed test locations separated by different distances and angles. Inputs corresponding to locations were presented to the network for 25 ms. The network activity was tested 900 ms after the input presentation. The stability of the network was measured by the distance between the vector of rates at 890 and 900 ms after input presentation. If the distance normalized by the length of the vector of activity at 890 ms was less than 1% the network was considered to be stable. The simulations showed that until a very high level of network corruption, 900 ms was sufficient for the network to stabilize. The values of p from 0 to 0.4 with the step 0.01 were tested. For each value of p, ten independent tests were run. For each test, a new set of weights was generated according to rule (5a) or (5b), and the network was run with the inputs corresponding to the same sequence of test locations. At each testing point, the normalized distances of the network activity from the activity of the "intact" tuned network were calculated. Failures to switch from representing one location to another revealed themselves as sharp increases both in the average and variance of normalized distances. The critical regions were double-checked by direct visualization of the maps of ensemble activity (e.g. FIG. 7).

Results

TTX Blocked Neural Discharge in the Injected Hippocampus for Hours

Discharge was recorded from dorsal hippocampus ~1 mm from the injection site (n=3). The simultaneous discharge in the ventral hippocampus (approx. AP 6, ML 5, DV 7) was also recorded. As expected, within 5-7 minutes of the injection, a time corresponding to the diffusion of TTX that was characterized in the midbrain, action potentials could not be detected at the dorsal site (FIG. 2A). Activity at the ventral site was silenced 30-40 minutes after injection. Activity at the ventral site returned suddenly after about 200 min. In contrast, activity at the dorsal site gradually increased starting about 240 min after the injection. Spontaneous firing at the dorsal site did not return to baseline values even after 7 hours. This demonstrates that TTX is an effective long-lasting neural activity blocker.

LFPs in the injected dorsal hippocampus were diminished at all frequencies immediately after TTX injection. It took about 1 hour for power in the gamma band to settle to its new steady state. From about 3 hours after the injection, power in the theta band began to restore (FIG. 2B). The injection only reduced LFPs in the ventral hippocampus on the injected side for about 10 minutes. Power then recovered and even increased between the theta and gamma frequencies (FIG. 2C).

Firing Rates in the Uninjected Hippocampus

Saline injection did not change firing rates (FIG. 3A) but TTX injection increased pyramidal cell discharge in the uninjected hippocampus if the cells were active before the injection. Pyramidal cells that were silent before the injection began to discharge (FIG. 3B). Wilcoxon comparisons of the rates in 250 ms bins 15 min before and up to 15 min after TTX was injected indicated that the rates of 41% of 73 pyramidal cells significantly increased. TTX increased the rates of units (n=63) that were active 5 min before TTX injection by 400%. Rates returned to baseline levels after 15 min ($F_{18,1197}=2.82$; $p=7.4\times10^{-5}$; FIG. 3B). Interneurons recorded on the same electrodes as pyramidal cells did not change their rates systematically. The changes in rate were independent of the simultaneously recorded LFP since power in the delta, theta, beta, gamma and ripple frequency bands did not change significantly during the recordings FIG. 3C).

Coactivity in the Uninjected Hippocampus

The TTX-induced activation of pyramidal cells in the uninjected hippocampus could have increased chances for pyramidal cells to discharge together. That could lead to a general increase of the connections amongst pyramidal cells because of activity-dependent plasticity mechanisms. This predicts that weak connections would strengthen more than already strong connections.

The central hypothesis of this study is that TTX injection impairs subgrouping by causing cognitive disorganization. The basis of the idea is the theory that cognitive coordination is manifest as synchronized coupling amongst neurons within a cell ensemble and uncoupled discharge of neurons from different ensembles. This reasoning predicts that to selectively impair subgrouping of representations while the representations themselves are preserved, cell pairs that fired independently before TTX injection should coactivate after the injection. The coactivity of simultaneously recorded pairs of cells is typically used to estimate the functional coupling of extracellularly recorded cells so Kendall's correlation between spike counts was calculated. Cell pairs with correlations below and above the median during the 15 min before TTX injection were taken to represent the initially "weak" and "strong" correlations, respectively. Correlations amongst the group of weakly correlated cell pairs tended to be $\leq 0.05$, a level indicating independent coupling of these cells.

Figure 4:
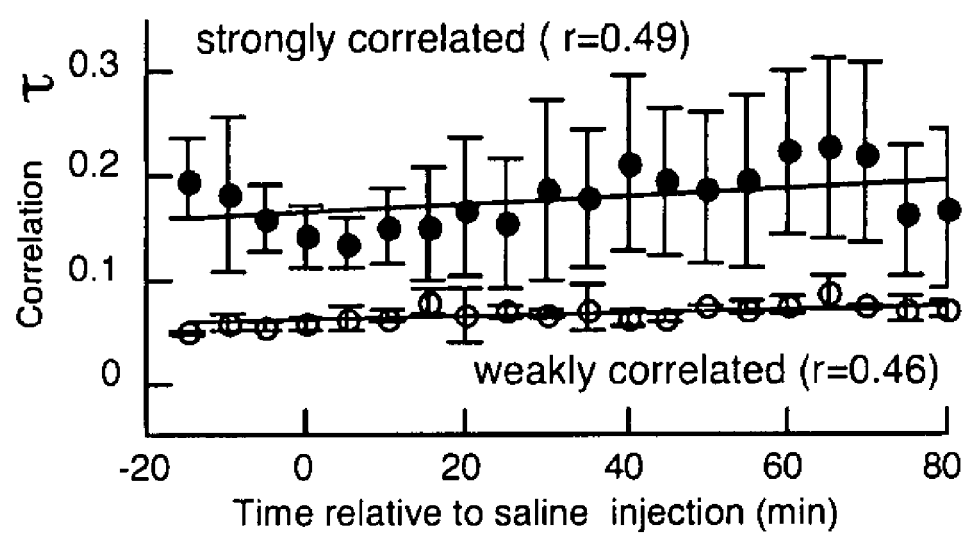
FIG. 4 provides a graphical representation of the effect of a saline control injection is not to change neural coactivity amongst principal cells in the un-injected hippocampus.
Figure 5:
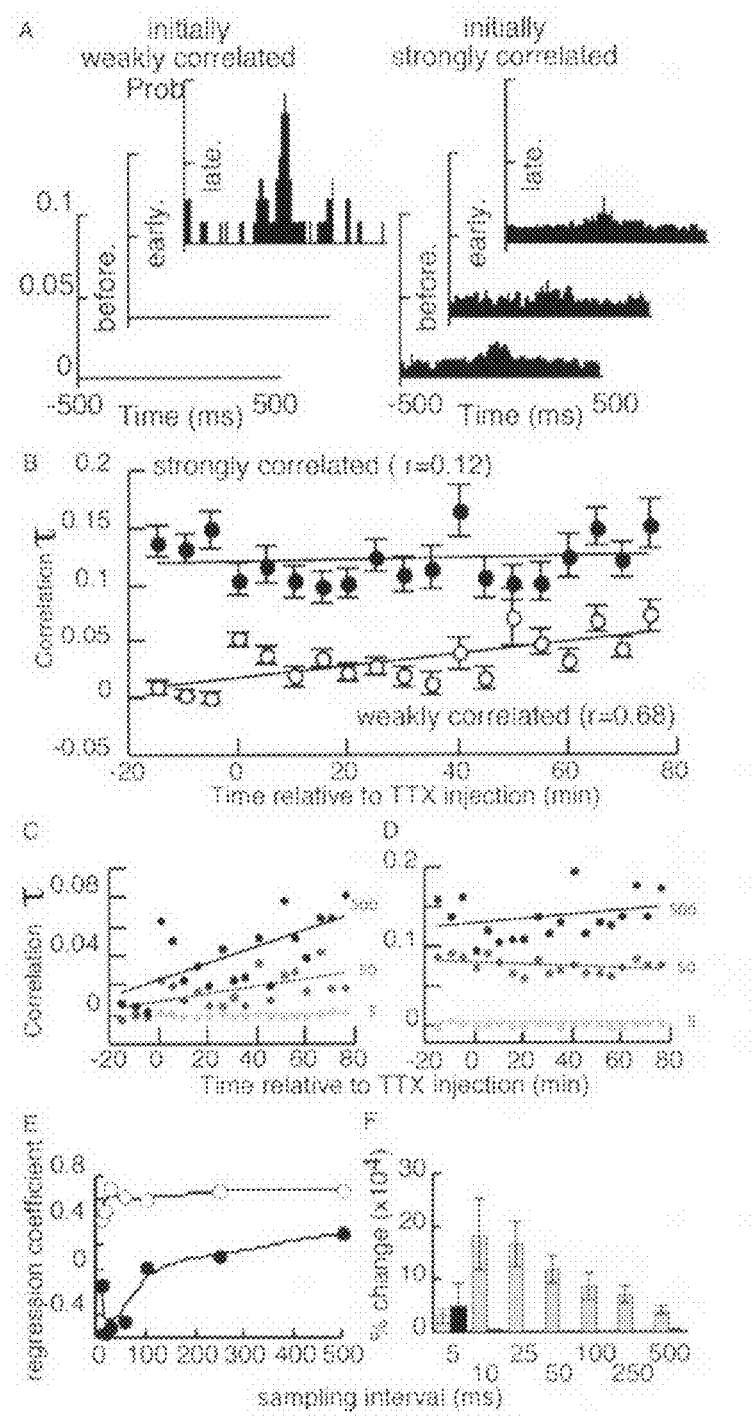
FIG. 5 provides a graphical representation of the effect that TTX injection changes neural coactivity amongst principal cells in the un-injected hippocampus.

Saline injection did not change either the initially weakly or strongly correlated cell pairs (FIG. 4) but TTX injection induced changes in accord with the hypothesis (FIG. 5). The initially weak correlations calculated at 250 ms became stronger and more variable about 40 min after TTX injection (FIGS. 5A, B; $F_{18,985}=6.10$, $p<3\times10^{-14}$). Dunnett's test indicated that the post-TTX correlations were significantly greater than the pre-TTX correlations immediately after and from 40 min and onwards except for the 45 min time point. In contrast, the initially strong correlations decreased in correspondence with the increased pyramidal firing. They then became more variable (FIGS. 5A, B; $F_{18,1203}=2.36$, $p=0.001$). Dunnett's test between the initially strongly correlated pairs indicated the correlations were lower only 5-20 min after TTX was injected. The increase of the initially weak correlations was modest because they only reached 57% of the initially strong correlations before injection. When all cell pair correlations were analysed together, the trend for correlations to increase was also significant ($F_{18,2207}=2.64$, $p=0.0002$) indicating regression to the mean does not account for the increase in the initially weakly correlated cell pairs.

Figure 6:
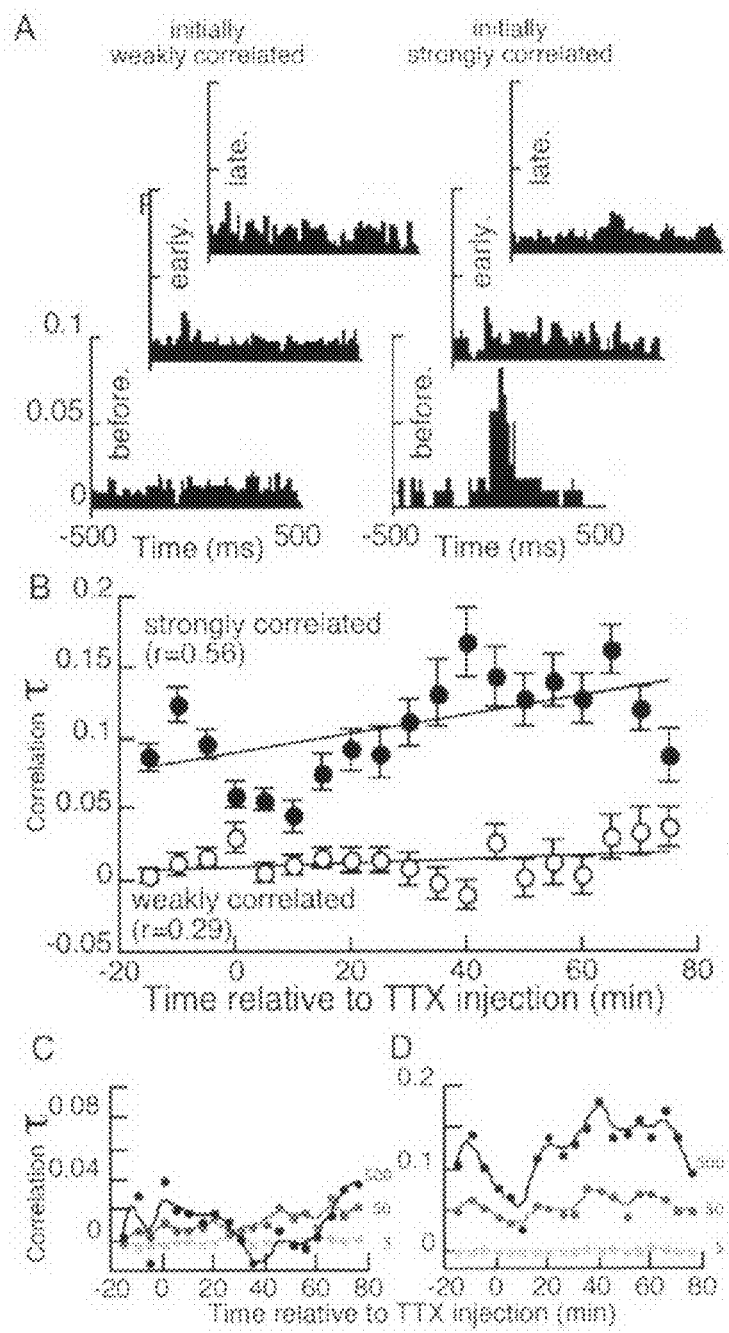
FIG. 6 provides a graphical representation of the effect that TTX injection transiently decreased correlations amongst the initially strongly correlated pairs of presumed pyramidal principle cells and inter-neurons in the un-injected hippocampus.

The correlations between the discharge of pyramidal cells and interneurons were also examined (FIG. 6). The initially weakly correlated pairs did not change ($F_{18,582}=1.35$, $p=0.15$) but the initially strongly correlated pairs decreased coactivity during the time corresponding to increased pyramidal cell firing ($F_{18,727}=5.11$, $p=4\times10^{-11}$). However, the only significant differences from the correlations before TTX were at 40 and 65 min when the values were increased.

Timescale of the TTX-Induced Coactivity

If the TTX-induced coactivity is related to gamma-based binding then the coactivity should manifest at the timescale of gamma. Furthermore, if the TTX-induced coactivity is related to the cognitive disorganization associated with disorganization in schizophrenia, one also expects the coactivity to manifest at the timescale of gamma since altered gamma is associated with schizophrenia and correlates with disorganization symptoms.

The timescale of the TTX-induced coactivity was estimated from the correlations at different sampling intervals. Since estimates of the correlation at individual time points are likely to be more inaccurate than estimates from many measurements, the average correlations for different time intervals, were fitted to a linear function of time and the functions were compared. The regression on the initially weak correlations was significant and positive for all sampling intervals (FIG. 5C). In contrast, the regressions on the initially strong correlations were only significant at short sampling intervals (10, 25, 50 ms) when they were negative (FIG. 5D).

If increased correlations were due to coactivation at a particular temporal resolution, then the regression should be weak at sampling intervals lower than the critical interval. The regression should suddenly increase for sampling intervals at the critical resolution and the increased regression would be maintained at longer sampling intervals. The pattern of the initially weakly correlated pairs of pyramidal cells resembled this expectation (FIG. 5E).

Place avoidance experiments demonstrated the TTX injection impaired subgrouping when behaviour was tested between 60 and 80 min. For each sampling interval, the relative change in the average correlation for each cell pair was calculated as the difference in the correlation during 60-80 min after TTX injection relative to the correlation before the injection. For statistical comparisons of these changes for different sampling intervals, this difference was normalized by the cell pair's pre-TTX correlation because the magnitude of the correlations increased with longer sampling intervals (see FIG. 5). In initially weakly correlated cell pairs the relative increase in correlations was several fold at sampling intervals greater than 5 ms (FIG. 5F; $F_{6,425}=2.85$; $p<0.01$). The largest changes of correlation were for the sampling intervals corresponding to gamma periods (10-50 ms). In contrast, the initially strong correlations were unchanged ($F_{6,528}=1.43$; $p>0.2$).

When all cell pairs were considered together there was a strong inverse relationship between the pre-TTX (−15 to 0 min) correlation of a cell pair and the change of this correlation 60 to 80 min after the injection. This is because cell pairs with initially weak correlations changed their correlations while pairs with initially strong correlations did not change. This inverse relationship was observed for all sampling intervals (range of Pearson's coefficients: −0.52 to −0.62; p's<0.01). This was the basis of the rule (eq. 5b) for corrupting weights in the network simulations that were used to model the effects of the TTX injection in the next section.

The correlations between presumed pyramidal cells and interneurons were also calculated at different temporal resolutions. TTX did not induce monotonic changes so the regression and time-scale analyses were not performed. The initially weak correlations were relatively stable and did not reach a level different from chance (FIG. 6B). The decrease of the initially strong correlations immediately after the TTX injection was only observed for time intervals of 100 ms and greater (FIG. 6C). The 100 ms time scale matches the course of GABA-B mediated inhibition in hippocampus of the urethane-anesthetized rat.

How Increased Coactivity can Cause Symptoms of Disorganization

Why should increased coactivity amongst principal cells impair subgrouping and contextual modulation but spare representational memory and navigation? Coactivity may occur by increasing the common input to cell pairs. Alternatively, increased synaptic connections between cell pairs may also induce coactivity. Regardless of the mechanism, the increased correlation of discharge indicates that the functional coupling between cells increased, and this can be modeled by manipulating the connection weights in a Hopfield-type artificial neural network in which firing rates rather than spike times are simulated.

Figure 7:
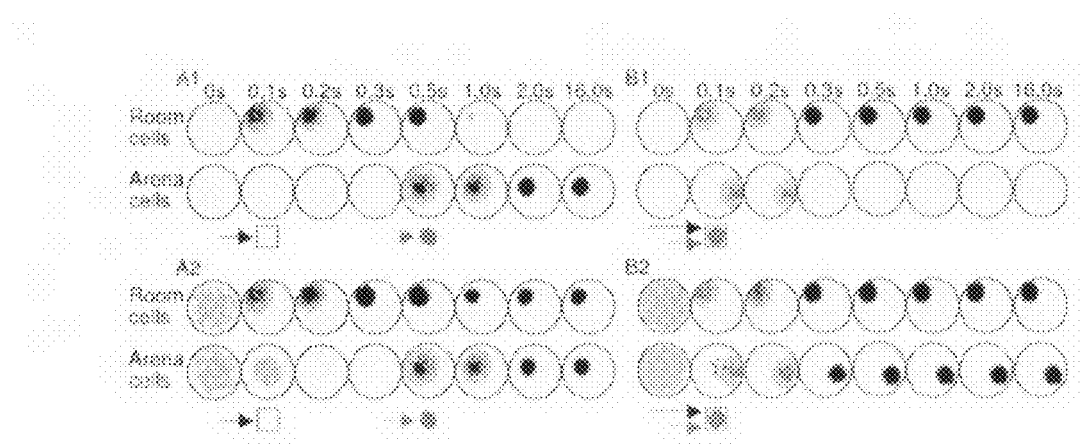
FIG. 7 provides network simulation illustrations that show randomly increasing excitatory-excitatory connections impaired sub-grouping of representations of room and arena locations.

A previously described Hopfield-type hippocampal network model was adapted to model subgrouping of stationary positions in the room and rotating positions in the arena. The model had two sets of competing attractor states corresponding to a representation of positions in the room and an independent representation of positions in the arena. Prior to any input the network activity was homogeneous and low (see t=0 s in FIG. 7). Momentary input corresponding to, for example, a location determined by room cues, induced an attractor state characterized by selective activation of the "room place cells"—the cells with localized firing defined with respect to room cues. This characteristic pattern of activation (the "activity packet") persisted in the absence of input, in accord with the definition of an attractor that activity converges to a steady and stable state in constant conditions (FIG. 7). Short, up to 25 ms, inputs corresponding to different locations within one frame (e.g. the room frame) quickly activated corresponding spatial representations (FIG. 7A1). Subsequent input corresponding to a position in the rotating arena caused the representation of the current room position to be replaced by the representation of the current arena position (FIG. 7B1), which was characterized by the selective activation of "arena place cells". Inputs corresponding to both room and arena positions caused the network to converge to represent only the stronger of the inputs (FIG. 7C1). The activation of either the representation of a room or arena position (but not both) demonstrates subgrouping and mimics normal place avoidance behaviour in that, moment to moment, the rat and network determine the current position in either the room or the arena, without confusing positions from the two frames.

Two models were considered for the increasing connection weights to explain the impairment in subgrouping associated with TTX-induced coactivity. The first model was based on the observation that the TTX injection caused a general increase of coactivity. It was assumed that all cell pairs could have been coactivated to an equal extent and with equal probability. A "general" corruption rule (Eq. 5a) was implemented to model this. Each connection weight was increased by a random number from the interval (0, p): $w_{ij}^{(1)}=w_{ij}+p\cdot\eta$; the maximum weight was limited to 1. First, the simulations were performed for the non-symmetric network. For $p\leq0.15$, as long as inputs were not dissociated, meaning as long as they were from positions within a single reference frame, for example the room, the network activity represented those positions as faithfully as the uncorrupted network (FIG. 7A2). When p=0.16 the network failed to represent a location within any frame; it converged to a parasitic attractor (data not shown). As in one study defined herein, a parasitic attractor as an attractor in which the network activity does not represent network inputs faithfully because the basin of attraction of such an attractor is so large that the system converges to the parasitic attractor state with high probability for many different inputs.

The second model was based on the observation of an inverse relationship between coactivity before the TTX injection and the change in coactivity caused by the injection. That observation suggested the main consequence of the TTX injection was to cause independent networks of neurons to fire together. That observation was implemented as a "selective" corruption rule (Eq. 5b). Accordingly, large weights were affected less than small weights. Because large weights in the model encoded the representation of positions within a frame, we expected that the network with weights corrupted according to Eq. 5b would be able to switch between location representations within one frame for values of p greater than 0.15. Indeed, as long as the inputs were already subgrouped to be from positions within either the room or the arena (compare FIGS. 7A1, 7A2), the network faithfully represented locations within a frame for $p\leq0.21$. When the connectivity was randomly increased between 0 and more than 21% of the connection's difference from the maximum value 1 (p>0.21 in Eq. 5b), the room input, while it was present, induced both a representation of the corresponding room position and some arena location that did not fade as in the case of p=0.2 (FIG. 7A2) but remained stable (not shown). The strengthened connectivity had its most dramatic effect on responses to dissociated room and arena inputs. FIG. 7B2 represents the typical behaviour of the selectively corrupted network with 0-20% increased weights. When room input was followed by arena input, the network converged to a pathological state with simultaneously active room and arena cells. When both the room and arena inputs were simultaneous, like the uncorrupted network, the network with 0-20% increased weights converged to represent only the stronger of the inputs. When the network weights were corrupted by 0-25% the network persistently represented both room and arena locations in response to simultaneous room and arena inputs (FIG. 7C2). Appropriate network behaviour was restored by increasing inhibition 9% (changing $w^{INH}$ from 0.32 to 0.35), predicting that mild doses of a GABA agonist like a benzodiazepine might attenuate the TTX-induced impairment of cognitive coordination.

The Importance of Corrupting Initially Weak Connection Weights

Since the coupling between independent representations should be low, the possibility that the subgrouping impairment was due to the increased coupling of cells that coded independent representations was considered. The network model to evaluate this idea was used because, unlike the hippocampus, in the model we could be certain that room-arena connections were between cells that code independent representations and that room-room and arena-arena connections were between cells that code the same representation. It was then selectively corrupted either only the between-representation connections or the within-representation connections and observed the effects on the network ability to switch from one representation to another ("subgroup") and to switch from representing one location to another in the same reference frame ("represent"). Networks with symmetric connection weights to minimize the dependence of the results of these experiments on the inhomogeneity of weights were used. The results are summarized in Table 1. The results were qualitatively the same after corrupting the network according to the general (Eq. 5a) or selective (Eq. 5b) corruption rules. Only the results of the selective rule is discussed herein and the results from both rules are reported in Table 1. In general, not surprisingly, the network could tolerate more corruption according to the selective rule than the general rule. Beyond a certain magnitude of corruption, in the absence of input, the network would spontaneously represent a location near the center of the space. These values of p's were used as the upper limit for corrupting the network in the experiments that follow.

To test if it was sufficient to corrupt the weights between room and arena cells to induce failures in subgrouping, the network was corrupted and then the weights between the pairs of room cells and between the pairs of arena cells were restored to the originally tuned values. Thus only the weights for pairs consisting of a room and an arena cell were left corrupted. These room-arena weights account for 50% of the network connections (53.2% of all the connections with weights at or below 0.25). This was sufficient to induce subgrouping failures when the magnitude of weight corruption was 0.15 or greater. It was not until the corruption was 0.24 or more that the network failed to switch from representing one location to another within one reference frame. Thus to selectively induce a subgrouping failure, it was sufficient to increase only the weights between room and arena cells.

It was then tested whether to induce subgrouping failures was necessary to increase the coupling between the room and arena cells. After corrupting the connection weights the weights between the pairs consisting of a room and an arena cell were restored to their initial (weak) values. There were no subgrouping or representation failures for magnitudes of corruption that were less than the level at which the network ceased to be stable prior to input. In summary, to induce a selective subgrouping deficit in the model, it was both necessary and sufficient to increase the connection weights between the initially weakly connected cells that encoded independent network representations.

It is stressed that both equations 5a and 5b produced qualitatively similar results. This is because the important corrupting change was to the weakly connected cells and both equations produced similar increases in these weights. The equations differed in how they affected the strongly connected cells, but increasing these weights did not selectively produce subgrouping failures.

Discussion

The TTX injection suppressed discharge in the injected hippocampus and altered discharge in the uninjected hippocampus. The first main finding is the TTX injection coactivated pyramidal cell pairs that initially discharged independently. In accord with temporal binding proposals and the definition of cognitive disorganization, altered firing rates did not accompany the coactivation. This result supports the hypothesis that impaired hippocampal cognitive coordination caused the TTX-induced impairment of subgrouping distal and local stimuli for place avoidance behaviour. The second main finding is the TTX-induced coactivity occurred at the timescale of gamma. This coactivity may represent failed segregation of cell assemblies and an index of the disorganization in schizophrenia. TTX-induced coactivity therefore has predictive validity as a model of the disorganization in schizophrenia. A second prediction, that the TTX-induced cognitive disorganization should selectively impair behaviour requiring subgrouping of relevant and irrelevant stimuli was already confirmed. While at face value, schizophrenia-associated neurobiology such as hippocampal inhibitory interneuron dysfunction, disinhibition induced by psychomimetics, hippocampal hyperactivity related to positive symptoms and altered functional relationships in schizophrenia seem related to the TTX experimental model.

Effect of Injecting TTX into One Hippocampus

Enough TTX to block neural activity should have diffused isotropically ~1 mm in 25 min. The TTX concentration would have been sub-effective within that volume by 200-300 min. The TTX blocked neural activity at a 1 mm distant CA1 site (FIG. 2) within a few minutes probably because intrahippocampal trisynaptic transmission was blocked at the injection site. The blockade lasted 4-5 hours as reported for the midbrain and extended to ventral hippocampal regions greater than 4.5 mm away. TTX injections of a twice-greater concentration were not effective beyond 1.5 mm suggesting the activity block of the ventral hippocampus was partly due to blocking the fimbria fibers within 1.5 mm of the injection. Ventral hippocampal LFPs were largely preserved (FIG. 2C), indicating these do not reflect spiking and that in the urethane-anesthetized rat intact perforant path and amygdala inputs were not sufficient to drive action potential discharge that was blocked 30-200 min after TTX injection. Since altered gamma (increased beta) in EEG is associated with disorganization it will be important to determine if the TTX-induced □ LFP oscillations in ventral hippocampus (FIG. 2C) index behavioural disorganization in rats.

The activity block of the injected hippocampus reduced commissural excitation of the uninjected hippocampus, which should have decreased feed-forward inhibition there. Indeed, in contrast to the persistent (>4 h) activity blockade in the injected hippocampus, firing rates changed transiently in the uninjected dorsal hippocampus. Presumed principal cells but not neighbouring interneurons increased firing for 15 minutes (FIG. 3). While increased pyramidal discharge is consistent with disinhibition, this was not reflected in unchanged interneuron rates in this or other studies of psychomimetic-induced disinhibition. Perhaps interneuron rates decreased in other layers, but the lack of change is more likely because the major excitatory input to interneurons after the injection was from the activated pyramidal cells. This pyramidal-interneuron feedback contributes to the strong homeostasis of hippocampal firing rates. The transient increase in pyramidal cell firing is consistent with firing rate homeostasis mediated by coupled excitation and inhibition. Initially coactive pyramidal and interneuronal cell pairs decreased their coactivity but only while pyramidal discharge rates were increased, suggesting the feedback had initially uncoupled and was then restored. Population rate constancy is a feature of attractor neural networks within which a balance between recurrent excitation and feedback inhibition operates to maintain network output in the presence of partial input.

TTX-Induced Cognitive Disorganization

Cognitive coordination is the set of processes that control spike times amongst neurons without affecting individual discharge properties like firing rates. One hour after TTX injection, spike timing between cells in the uninjected hippocampus was altered but firing rates were not. The TTX-induced coactivation of initially uncoupled pyramidal cell pairs was detected from ~40 min after TTX injection (FIG. 5). This is unlikely to reflect a process of regression-to-the-mean since 1) the increase was observed when all cell pairs were analysed together; 2) the increase of the initially weakly correlated cell pairs was delayed; 3) it was not accompanied by decreased correlations amongst initially highly correlated cell pairs; and 4) the pattern of correlation changes was not observed amongst pyramid-interneuron pairs.

Schizophrenic subjects, impaired in a gestalt task requiring perceptual grouping of visual stimuli, had reduced gamma and increased beta power in visual stimulus-evoked oscillations in the parietal and occipital EEG. These data add to the growing consensus that disturbed neural coordination at gamma (and beta) frequencies may underlie disorganized processing in different sensory modalities during sleep and rest. This predicts the TTX-altered coactivity would occur at gamma frequencies if it reflects a schizophrenia-related phenomenon. Consistent with this idea, the TTX-induced coactivity between pyramidal cells emerged and was maximal at gamma periods (FIGS. 5E, F).

While the initially uncoupled cell pairs increased 10-50 ms coactivity, the initially strongly correlated pairs significantly, and specifically decreased 25-50 ms coactivity (FIG. 5). Although there was a consistent tendency for reduced gamma in the hippocampal LFP at the time of the behavioural impairment (60-80 minutes post-injection), the trend was not significant. While increased beta oscillations were not observed in dorsal hippocampal LFPs (FIG. 3) they were observed in the ventral hippocampus (FIG. 2C), which has direct connections to the prefrontal circuits thought to be affected in schizophrenia. Assuming that gamma synchrony is important for hippocampal information processing the selective disorganization of this coactivity in the uninjected hippocampus may underlie the TTX-induced behavioural impairment of subgrouping.

Increased coactivity in the uninjected hippocampus was independent of firing rate changes, and specific to the discharge of the presumed pyramidal cell pairs that initially fired independently. The specificity of the altered correlations precludes explanations for the increases based on the duration of anaesthesia, altered rates or boundary effects. The pyramidal cell coactivity was the TTX-induced change in the uninjected hippocampus that persisted at the time of the behavioural impairment of place avoidance requiring subgrouping. Since these alterations were observed under anaesthesia they cannot be consequences of TTX-induced perceptual, sensorimotor, or behavioral alterations. An important next step is to record the effects of the TTX injection in behaving animals. There are strong positive and negative firing covariations in place cell pairs with overlapping firing fields and the cognitive disorganization hypothesis predicts selective alterations of the covariance. Nonetheless, the urethane-anaesthetized preparation provides a means for a high throughput neurophysiological assay that may be valuable for drug discovery.

How TTX-Induced Coactivity can Cause Disorganization Symptoms

The modeling explains that increased coactivation of weakly coupled principal cells can selectively produce disorganization. Additional studies are required to determine whether TTX-induced disinhibition or indiscriminate synaptic potentiation caused the coactivity. Regardless of the cause, the result was increased functional coupling. A severe general increase of coupling in the model (Eq. 5a) impaired activation of the stored representations, analogous to the impaired retrieval of spatial memory caused by globally saturating LTP at hippocampal synapses. However the disturbing effect was only because the connection between initially weakly coupled cells had increased. It is an important general result that increasing the coupling of the initially weakly coupled elements in the model, specifically those between cells coding independent representations was necessary and sufficient to impair segregated activation of stored representations without altering retrieval of the representations themselves (FIG. 7; Table 1). Dissociating inputs to the corrupted network caused it to respond inappropriately, as if there was stimulation from both reference frames. This defines a parasitic attractor, a pathological steady and stable state of activity that does not reflect reality and is used to model hallucinations.

These data suggest a model for cognitive disorganization where hippocampal patterns of response fail to segregate in accord with what is relevant and irrelevant. However, cognitive disorganization would arise not merely because the information content of hippocampal output is inappropriate. Disorganization would manifest because the increased coactivity of hippocampal output will exert altered feed-forward inhibitory control of prefrontal and possibly accumbal circuits. Preliminary 2-deoxyglucose-glucose imaging indicates the TTX injection induced hypometabolic changes in ventral hippocampal and prefrontal networks. This would further disturb the coordination of cognitive representations.

The figures are now discussed in further detail to describe the present invention. As described above, FIG. 1 is an example used to illustrate subgrouping and contextual modulation. If the goal is to identify a word, one segregates the irrelevant numbers 12 and 14 from the other symbols and groups the relevant letters with the central symbol interpreted as a "B" to form the word "cable". The meaning of the central symbol as a number or a letter is determined by the context in which it is being interpreted. FIG. 2, shows the effect of unilateral TTX injection on the injected hippocampus. (A) TTX blocked extracellular activity in the injected hippocampus. This recording from dorsal CA1 was made 0.7 mm posterior, 0.7 mm lateral, and 0.3 mm dorsal to the injection site. The recording from ventral hippocampus was made 2 mm posterior, 2.5 mm lateral and 3.4 mm ventral to the injection site. The threshold for recording an event was set to 39 µV on all tetrode channels. A) Tetrode energy measures the instantaneous activity detected by a tetrode. It was defined as the sum of the areas under the four-tetrode waveforms. The tetrode energy is plotted for each event as a function of time relative to TTX Injection. Vertical line 1 indicates insertion of the injection needle. Lines 2 and 3 indicate the start and end of the TTX infusion. Line 4 indicates when the dorsal electrode was moved (10 µm) to mechanically stimulate hippocampus. The robust response to mechanical stimulation indicates that although spontaneous discharge in the dorsal hippocampus was limited 7 hours after TTX injection, action potentials could be evoked. The local field potentials (LFP) recorded at the dorsal B) and ventral C) sites are presented in spectragrams. TTX immediately attenuated LFPs at most frequencies in the dorsal site; frequencies took about 1 hour to reach the reduced steady state level. In the ventral site, except immediately after injection, TTX did not attenuate LFPs. In fact starting at about 40 min after injection power increased in the beta (10-25 Hz) band.

FIG. 3 shows the effects of unilateral saline and TTX injection on the uninjected hippocampus. A) Average 2 ms tetrode waveforms from an interneuron and pyramidal cell illustrate a characteristic difference in the durations of the sodium spike (calibration bar indicates duration on the largest waveform: inh: 325 μs; pyr: 552 μs). Voltage calibration bars 125 μV. Firing rates of units that were active from −5 to 0 min were normalized by the rate in that interval. Saline injection did not alter firing rates. (inset B) Raster representation of simultaneously recorded cells during four 2-min episodes. The injection did not change the firing of presumptive interneurons (inh; gray) but presumptive pyramidal cells (pyr; black) dramatically and transiently increased their discharge. B) Presumptive pyramidal cells increased their discharge almost immediately for about 15 min (p's<0.05 relative to −5 min). Presumptive inter-neurons did not change their rates. C) The relative power in the delta, theta, beta, gamma and ripple frequency bands did not change during the recordings.

FIG. 4 shows that the saline injection did not change coactivity in the uninjected hippocampus. Coactivity was measured by the Kendall correlation $\tau$ of spike counts in 250 ms bins between 52 pairs of presumed pyramidal cells recorded from 4 rats. Pairs with pre-injection correlations below and above the median correlation were classified as weakly and strongly correlated, respectively. Where as FIG. 5 shows that the TTX injection changed correlated discharge in the uninjected hippocampus. (A) Cross correlograms that clearly illustrate the changes that were typical for weakly and strongly correlated cell pairs are given for the 15 minutes before, immediately after (early) and from 60-80 min (late) after TTX injection. Correlations for these histograms were calculated at 250 ms resolution. Before injection, the strongly correlated pair's correlation was quantified by $\tau$=0.18. Immediately after injection it decreased ($\tau$=0.08) and then later it recovered ($\tau$=0.24). The weakly correlated pair was uncorrelated before ($\tau$=−0.004) and early after ($\tau$=−0.009) injection but an hour later it had substantially increased ($\tau$=0.15). (B) The Kendall correlation $\tau$ of spike counts in 250 ms bins between pairs of presumed pyramidal cells. Pairs with pre-TTX correlations below and above the median correlation were classified as weakly and strongly correlated, respectively. TTX increased the correlation in the weakly correlated pairs immediately after the injection and from about 40 min and onwards. The correlations of the initially strongly correlated pairs decreased transiently when pyramidal firing rates were increased. Linear regression lines and the regression coefficients are given. (C, D) Timescale analyses of the changes in correlated discharge between presumed pyramidal cells in the uninjected hippocampus. The correlated discharge of (C) the weakly and (D) strongly correlated pairs of cells were characterized each five minutes for different sampling intervals from 5 to 500 ms (only 5, 50, 500 ms intervals shown). The change in the correlations as a function of the time relative to TTX injection is represented by the regression line for each sampling interval. The weakly correlated pairs had positively sloped regression lines while the strongly correlated pairs had negative or flat regression lines. (E) The regression coefficients from C, D plotted as a function of the sampling interval. Weakly correlated pairs (open symbols) had increased regression coefficients at 25 ms and longer, while it was reduced in the strongly correlated pairs (closed symbols) at 10-50 ms. (F) The relative change of the correlation averaged from 60 to 80 min after TTX injection relative to the correlation averaged from 15 to 0 min before TTX injection plotted as a function of sampling interval. The weakly correlated pairs were generally increased several fold, and the strongly correlated pairs were not increased. The increase in the correlations at 10-50 ms sampling intervals were greater than at the 5 ms interval (Dunnett's one-tail tests) suggesting that the increase of correlated discharge was predominantly at the timescale of gamma.

FIG. 6 shows the correlations between presumed pyramidal cells and interneurons decreased transiently for the initially strongly correlated pairs. The pattern of change corresponded to the changes between the initially strongly connected pairs of pyramidal cells (FIG. 5). The correlations between the initially weakly correlated pairs did not change. (A) Cross correlograms that clearly illustrate the changes that were typical for weakly and strongly correlated cell pairs are given for the 15 minutes before, immediately after (early) and from 60-80 min (late) after TTX injection. The strongly correlated pair's correlation before injection ($\tau$=0.12) decreased immediately after injection ($\tau$=0.02) and 60 min later it was restored ($\tau$=0.10). The weakly correlated pair ($\tau$=0.01) was about the same early ($\tau$=0.01) and late ($\tau$=0.009) after injection. (B) The Kendall correlation $\tau$ of spike counts in 250 ms bins between pairs of presumed pyramidal and inhibitory cells. Pairs with pre-TTX correlations below and above the median correlation were classified as weakly and strongly correlated, respectively. TTX did not change the correlation in the weakly correlated pairs. The correlations of the initially strongly correlated pairs decreased transiently when pyramidal firing rates were increased. Linear regression lines and the regression coefficients are given. (C, D) Timescale analyses of the changes in correlated discharge between presumed pyramidal cells and interneurons in the uninjected hippocampus. The correlated discharge of (C) the weakly and (D) strongly correlated pairs of cells were characterized each five minutes for different sampling intervals from 5-500 ms (only 5, 50, 500 ms shown). The time courses of the changes are highlighted by a smooth fit of the data for each sampling interval. The weakly correlated pairs had no tendency to change, but at intervals of 100 ms or greater, the strongly correlated pairs decreased for about 15 min after TTX injection.

FIG. 7 shows that network simulations illustrate that randomly increasing excitatory-excitatory connections impaired subgrouping of representations of room and arena locations. Location-specific ensemble activity is represented as an activity packet. Each set of maps represents the ensemble activity of the room cells (upper row) and the arena cells (lower row) at the indicated moment of time. Activity is represented by a 5-level colour scale (maximum values dark blue to red are: 0; 0.125; 0.375; 0.5; 1). Room inputs (green arrow and square) and arena inputs (blue arrow and circle) to the network correspond to the "rat" location in the corresponding spatial frame. The arrow lengths represent the magnitude of inputs. (A) Response to serial inputs from the same frame. Short, up to 25 ms, inputs corresponding to different locations within one frame quickly activated corresponding spatial representations both in the (A1) "intact" network and (A2) the network with 0-20% corrupted weights. (B) Response to serial inputs from different frames. At 0.1 s a room location in the northwest provided room input for 25 ms. This induced a corresponding frame-specific, location-specific activity bump only in the room frame, which persisted after the input was removed. Later, at 0.5 s a dissociated arena input was presented for 25 ms. B1) the network switched from representing the room location to representing the arena location. B2) After increasing connection weights, the experiment was repeated. The network was less stable and developed a merged parasitic attractor. The room input was faithfully represented by room cells, but a subset of arena cells was also activated. The room activity persisted after the arena input was presented so both the room and arena locations were simultaneously and persistently activated. (C) Response to parallel inputs from different frames. At 0.1 s strong input corresponding to a room location and weaker input corresponding to an arena location were simultaneously presented for 25 ms. When the inputs ceased (C1) only the stronger room input was persistently represented (C2) but both locations were simultaneously and persistently represented in the network with increased connectivity.

Finally, Table 1 shows the simulation results suggesting that corrupting connection weights between room and arena cells is necessary and sufficient to induce selective subgrouping failures.

TABLE 1

| Corruption rule General: Eq. 5a Selective: Eq. 5b | Corrupted weights | Maximal tolerated corruption | Critical p for representation failures | Critical p for subgrouping failures |
| --- | --- | --- | --- | --- |
| General | room-arena | p = 0.21 | p ≧ 0.21 | p ≧ 0.13 |
| Selective | room-arena | p = 0.24 | p ≧ 0.24 | p ≧ 0.15 |
| General | room-room and arena-arena | p = 0.22 | no failures for p ≦ 0.22 | no failures for p ≦ 0.22 |
| Selective | room-room and arena-arena | p = 0.32 | no failures for p ≦ 0.32 | no failures for p ≦ 0.32 |

While the present invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof.

What is claimed is:

1. An in vivo high throughput assay method for identifying a candidate agent having anti-psychotic properties comprising:
   a) adding an effective amount of neural activity blocker to a first portion of a hippocampus of an animal subject, said first portion of said hippocampus being substantially opposite from a second portion of said hippocampus having extra-cellular recording electrodes positioned therein for recording discharge of an ensemble of neurons;
   b) continuously recording neural activity in said second portion of said hippocampus for a predetermined amount of time before and after step a);
   c) administering a predetermined amount of at least one candidate agent to said animal subject either directly to the brain, or indirectly by oral administration or by systemic injection during a predetermined period of time either before step a) or after step a), depending on the candidate agent's presumed properties;
   d) measuring the number of neurons in said second portion of said hippocampus that discharge coactively after adding said effective amount of neural activity blocker to said first portion of said hippocampus and after adding said candidate agent of step c) to said animal subject;
   e) measuring the probability of neurons in said second portion of said hippocampus that discharge coactively after adding said effective amount of neural activity blocker to said first portion of said hippocampus; and
   f) correlating a decrease in the probability of neurons firing coactively as determined in step e) with a candidate agent having anti-psychotic properties.

2. The high throughput assay method for identifying a candidate agent having anti-psychotic properties of claim 1 wherein said neural activity blocker is selected from the group consisting of tetrodotoxin (TTX), muscimol, lidocaine, and other local anesthetics.

3. The high throughput assay method for identifying a candidate agent having anti-psychotic properties of claim 2 wherein said neural activity blocker is tetrodotoxin (TTX).

4. The high throughput assay method for identifying a candidate agent having anti-psychotic properties of claim 3 wherein about 5 ng of TTX in a physiological solution is administered to said first portion of said hippocampus.

5. The high throughput assay method for identifying a candidate agent having anti-psychotic properties of claim 4 wherein said physiological solution containing TTX is added to a precise location in said first portion of said hippocampus.

6. The high throughput assay method for identifying a candidate agent having anti-psychotic properties of claim 1 wherein a correlation calculation is used to measure the coactivity of neuronal discharge before and after adding said candidate agent to said first portion of said hippocampus.

7. The high throughput assay method for identifying a candidate agent having anti-psychotic properties of claim 6 wherein the correlation calculation is performed using the Pearson correlation calculation technique, the Kendall correlation calculation technique or the arbitrary variants of any mathematical correlation technique.

8. The high throughput assay method for identifying a candidate agent having anti-psychotic properties of claim 1 wherein said animal subject is anesthetized.

9. The high throughput assay method for identifying a candidate agent having anti-psychotic properties of claim 1 wherein said animal subject is a rat.

10. The high throughput assay method for identifying a candidate agent having anti-psychotic properties of claim 9 wherein said rat is a Long-evans rat.

11. The high throughput assay method for identifying a candidate agent having anti-psychotic properties of claim 8 wherein said animal subject is deeply anesthetized with an injection comprising a solution containing 125 g/kg 20% urethane.

12. An in vivo method of inducing and measuring neural activity normally associated with a psychotic state comprising:
   a) adding an effective amount of neural activity blocker to a first portion of a hippocampus of an animal subject, said first portion of said hippocampus being substantially opposite from a second portion of said hippocampus having extra-cellular recording electrodes positioned therein for recording discharge of an ensemble of neurons;
   b) continuously recording neural activity in said second portion of said hippocampus for a predetermined amount of time before and after step a);
   c) measuring the number of neurons in said second portion of said hippocampus that discharge coactively after adding said effective amount of neural activity blocker to said first portion of said hippocampus; and
   d) correlating an increase of the number of neurons that discharge coactively as determined in step c) with an induced psychotic state.

13. The method of inducing and measuring neural activity normally associated with a psychotic state of claim 12 wherein said neural activity blocker is selected from a group consisting of tetrodotoxin (TTX), muscimol, lidocaine and other local anesthetics.

14. The method of inducing and measuring neural activity normally associated with a psychotic state of claim 12 wherein said animal subject is anesthetized.

15. The method of inducing and measuring neural activity normally associated with a psychotic state of claim 14 wherein said animal subject is a rat.

16. The method of inducing and measuring neural activity normally associated with a psychotic state of claim 14 wherein said animal subject is deeply anesthetized with an injection comprising a solution containing 125 g/kg 20% urethane.

* * * * *